US005604101A

United States Patent [19]

Hanley et al.

[11] Patent Number: 5,604,101

[45] Date of Patent: Feb. 18, 1997

[54] METHOD OF MINIMIZING CONTAMINATION IN AMPLIFICATION REACTIONS USING A REACTION TUBE WITH A PENETRABLE MEMBRANE

[75] Inventors: Kathleen A. Hanley, Gurnee, Ill.; A. David Hofferbert, Grafton, Wis.; Helen H. Lee, Lake Forest, Ill.; Curtis J. Pepe, McHenry, Ill.; Thomas F. Zurek, River Forest, Ill.

[73] Assignee: Abbott Laboratories, Abbott Park, Ill.

[21] Appl. No.: 559,932

[22] Filed: Nov. 17, 1995

Related U.S. Application Data

[63] Continuation of Ser. No. 140,632, Oct. 22, 1993, abandoned.

[51] Int. Cl.[6] .............................. C12Q 1/68; C12P 19/34

[52] U.S. Cl. .............................................. 435/6; 435/91.2

[58] Field of Search ........................ 435/6, 91.2; 422/100, 422/101, 102; 215/247, 249, 250, 258, 354

[56] References Cited

U.S. PATENT DOCUMENTS

| | | | |
|---|---|---|---|
| 4,720,385 | 1/1988 | Lembach | 424/86 |
| 4,721,137 | 1/1988 | Müller | 141/65 |
| 4,830,209 | 5/1989 | Jessop et al. | 215/273 |
| 4,874,102 | 10/1989 | Jessop et al. | 215/273 |
| 4,896,780 | 1/1990 | Jessop et al. | 215/291 |
| 4,953,741 | 9/1990 | Jessop et al. | 220/273 |
| 4,956,103 | 9/1990 | Jessop et al. | 210/787 |
| 5,221,608 | 6/1993 | Cimino et al. | 435/6 |
| 5,229,297 | 7/1993 | Schnipelsky et al. | 436/94 |
| 5,364,591 | 11/1994 | Green et al. | 422/58 |

OTHER PUBLICATIONS

Lau et al., *Anal. Biochem.* 110, 144–145 (1981).

*Primary Examiner*—Kenneth R. Horlick
*Attorney, Agent, or Firm*—Thomas D. Brainard; Paul D. Yasger

[57] ABSTRACT

A disposable reaction vessel for performing nucleic acid amplification assay. The disposable reaction vessel has a penetrable cap that can be penetrated by an automated pipettor to aspirate a portion of an amplified reaction product. The disposable reaction vessel contains the reagents necessary to perform a nucleic acid amplification assay. A patient specimen is added to the unit dose reagents in the disposable reaction vessel and the penetrable cap is closed. The disposable reaction vessel containing the reaction mixture and the specimen undergoes amplification, typically by placing it in a thermal cycler. After amplification the intact disposable reaction vessel is transferred to an automated analyzer where an automated pipettor penetrates the closure membrane and aspirates a portion of the amplified sample for further processing, without removal of the reaction vessel cap. This avoids the generation of potentially contaminating aerosols or droplets.

12 Claims, 4 Drawing Sheets

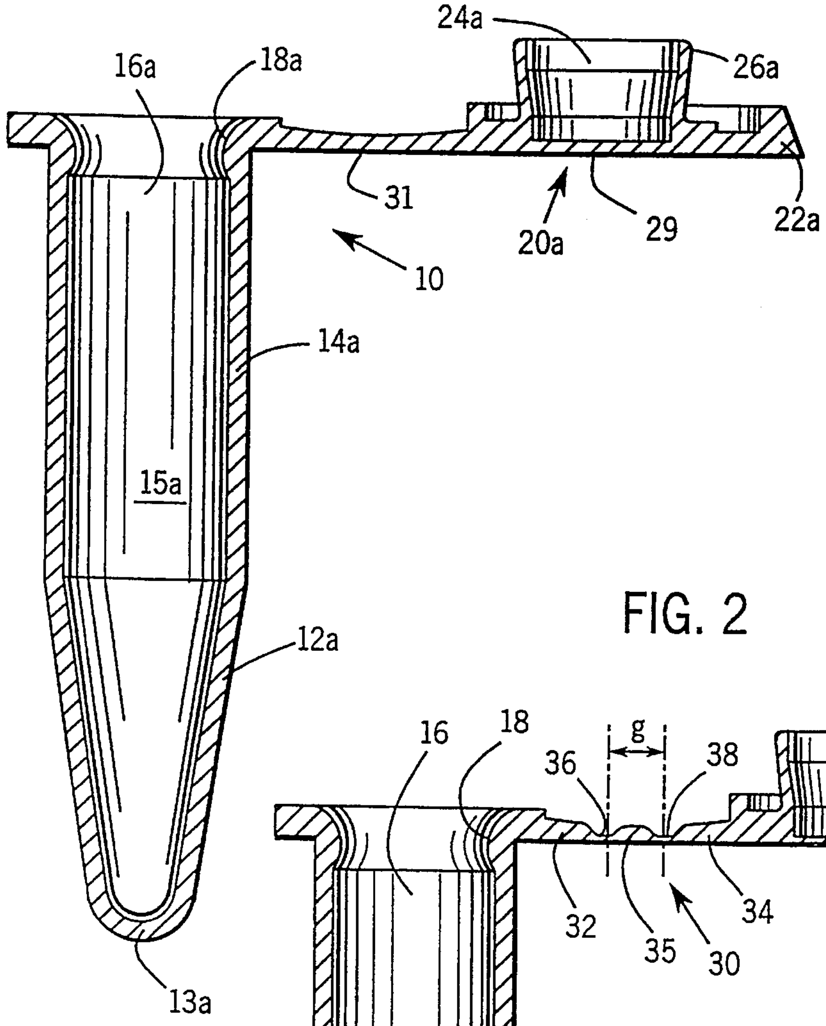
FIG. 1
PRIOR ART
FIG. 2
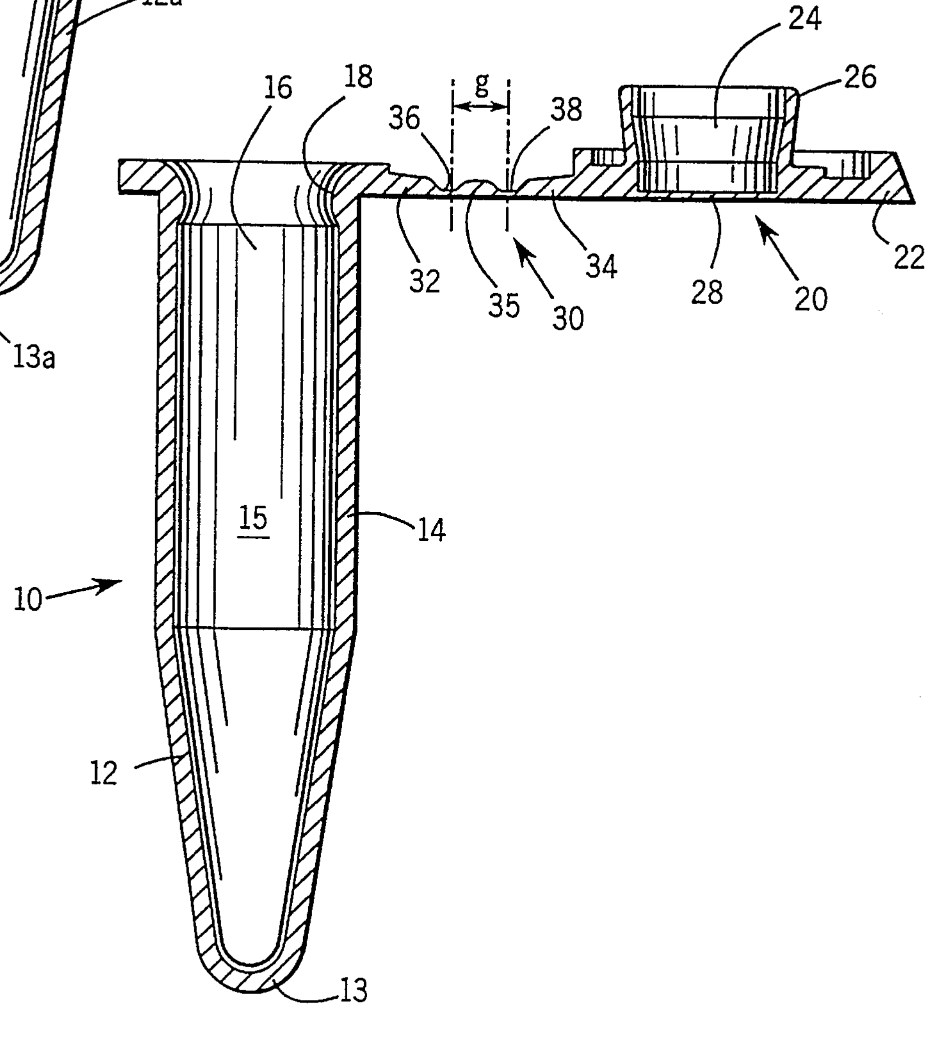

FIG. 3
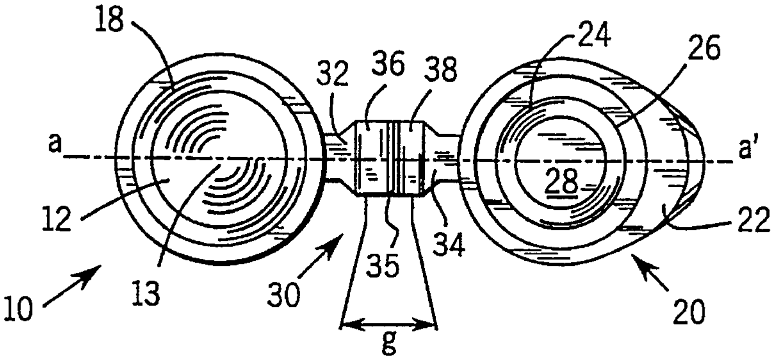
FIG. 4
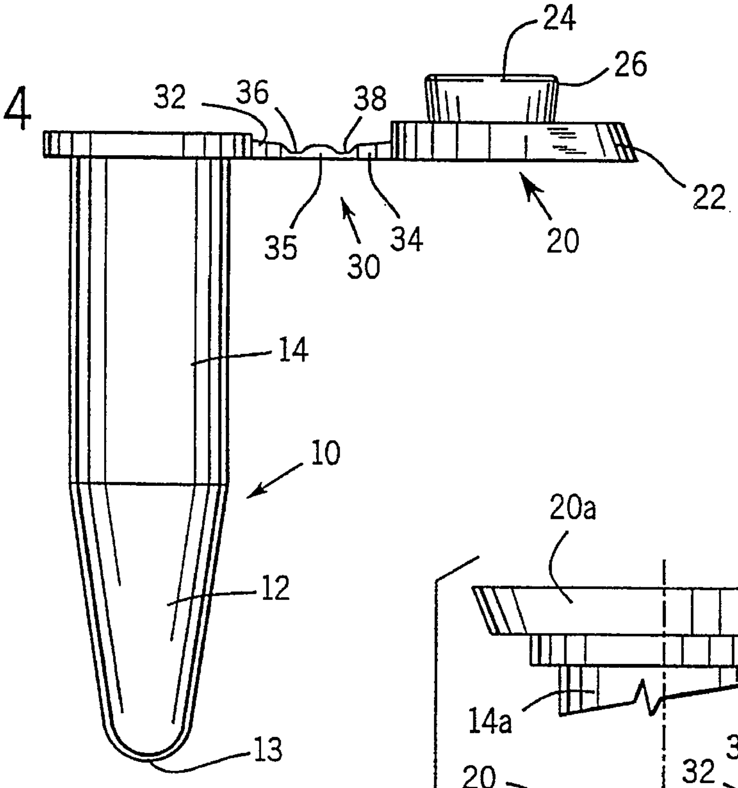
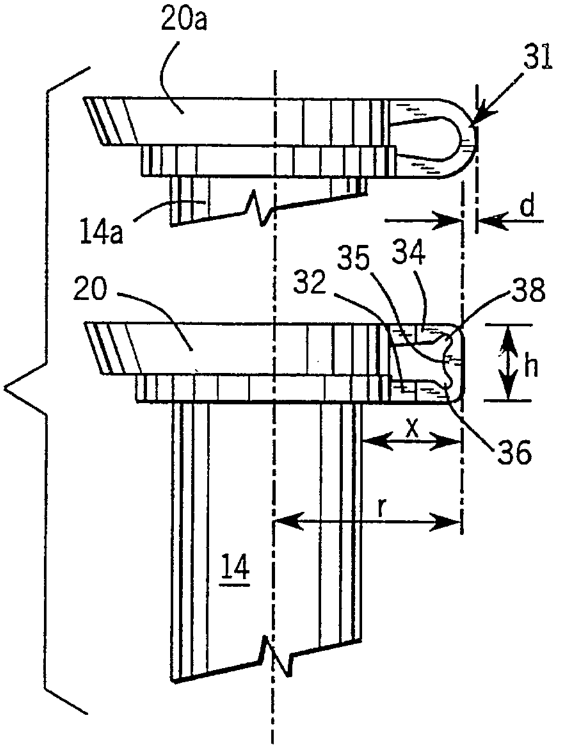
FIG. 5

METHOD OF MINIMIZING CONTAMINATION IN AMPLIFICATION REACTIONS USING A REACTION TUBE WITH A PENETRABLE MEMBRANE

This application is a continuation of U.S. patent application Ser. No. 08/140,632, filed Oct. 22, 1993, abandoned.

This invention relates to reaction tubes suitable for amplification reactions and, in particular, to tubes for use in automated thermal cycling and detection instruments. The invention also relates to methods for automated use of such tubes.

This application is related to co-owned U.S. application Ser. No. 08/141,243, now abandoned, filed on even date herewith, entitled Tube Transport System and Method of Use.

BACKGROUND OF THE INVENTION

Amplification techniques for the detection of target nucleic acids in biological samples offer high sensitivity and specificity for the detection of infectious organisms and genetic defects. Copies of specific sequences of nucleic acids are synthesized at an exponential rate through an amplification process. Examples of these techniques are the polymerase chain reaction (PCR), disclosed in U.S. Pat. Nos. 4,683,202 and 4,683,195 (Mullis); the ligase chain reaction (LCR) disclosed in EP-A-320 308 (Backman et al); and gap filling LCR (GLCR) or variations thereof, which are disclosed in WO 90/01069 (Segev), EP-A-439-182 (Backman, et al), GB 2,225,112A (Newton, et al) and WO 93/00447 (Birkenmeyer et al.). Other amplification techniques include Q-Beta Replicase, as described in the literature; Strand Displacement Amplification (SDA) as described in EP-A-497 272 (Walker), EP-A-500 224 (Walker, et al) and in Walker, et al., in *Proc. Nat. Acad. Sci. U.S.A.*, 89:392 (1992); Self-Sustained Sequence Replication (3SR) as described by Fahy, et al. in PCR Methods and Applications 1:25 (1991); and Nucleic Acid Sequence-Based Amplification (NASBA) as described in the literature.

These reactions, particularly where requiring thermal cycling, are usually carried out in microfuge-type tubes such as the SlickSeal™ tubes available from National Scientific (San Rafael, Calif.), or in Thin-Walled GeneAmp™ tubes available from Perkin-Elmer (Norwalk, Conn.). Another type of reaction container is a strip of microfuge reaction vessels combined with a strip of domed caps as described in EP-A-488 769 and marketed by Perkin-Elmer (Norwalk, Conn.) as MicroAmp™ for use with a Perkin-Elmer 9600 thermal cycler. In a typical procedure, after performing the amplification reaction the tubes are opened and a portion of the amplified reaction product is transferred to a detection apparatus such as a microtiter plate, a gel or other detection apparatus.

A major problem with such nucleic acid amplification procedures is the contamination risk when the amplification vessels are opened up. Spillage, droplet formation and/or aerosols can be generated when the caps are removed in order to remove a portion of the amplified reaction product for detection analysis. This can spread the amplified product throughout the lab by airborne droplets or on equipment and can contaminate un-amplified samples and/or reagents. This will quickly lead to false positive results. Extreme precautions must be taken to prevent such contamination. Physical separation between sample preparation, amplification and detection areas has been customarily used in the art. It is quite cumbersome, expensive and requires rigorous training to prevent transfer of lab coats, gloves, pipettes or laboratory equipment between such segregated areas.

U.S. Pat. No. 5,229,297 and corresponding EP-A- 0 381 501 (Kodak) disclose a cuvette for carrying out amplification and detection of nucleic acid material in a closed environment to reduce the risk of contamination. The cuvette is a closed device having compartments that are interconnected by a series of passageways. Some of the compartments are reaction compartments for amplifying DNA strands, and some of the compartments are detection compartments having a detection site for detecting amplified DNA. Storage compartments may also be provided for holding reagents. Samples of nucleic acid materials, along with reagents from the storage compartments, are loaded into the reaction compartments via the passageways. The passageways leading from the storage compartment are provided with one-way check valves to prevent amplified products from back-flowing into the storage compartment. The sample is amplified in the reaction compartment, and the amplified products are transferred through the interconnecting passageways to detection sites in the detection compartment by applying external pressure to the flexible compartment walls to squeeze the amplified product from the reaction compartments through the passageways and into the detection compartments. Alternatively, the cuvette may be provided with a piston arrangement to pump reagents and/or amplified products from the reaction compartments to the detection compartment.

Although the cuvette disclosed in EP 0 381 501 A2 (Kodak) provides a closed reaction and detection environment, it has several significant shortcomings. For example, the multiple compartments, multiple passageways, check valves and pumping mechanisms present a relatively complicated structure that requires much effort to manufacture. Also, the shape and configuration of the cuvette disclosed in EP 0 381 501 A2 do not allow it to be readily inserted into conventional thermal cycling devices. In addition, the fluid transfer methods utilized by the cuvette call for a mechanical external pressure source, such as a roller device applied to flexible side walls or the displacement of small pistons. Conventional thermal cycling devices are not readily adapted to include such external pressure sources, and mechanical pressure applied to the flexible walls can rupture these walls, especially if the cuvette is misaligned. Rupture of the flexible wall of an external compartment containing the amplified reaction product would lead to contamination of the inside of the instrument and possibly the entire laboratory. Finally, the apparatus described in this reference is quite limited in terms of throughput of the disclosed devices. The system does not provide the desired flexibility for manufacturing.

French patent publication No. FR 2 672 301 (to Larzul) discloses a similar hermetically closed test device for amplification of DNA. It also has multiple compartments and passages through which sample and/or reagents are transferred. The motive forces for fluid transport are described as hydraulic, magnetic displacement, passive capillarity, thermal gradient, peristaltic pump and mechanically induced pressure differential (e.g. squeezing).

Other methods applied in the art to deal with contamination issues are chemical in nature. One such method is described in U.S. Pat. No. 5,035,996 (Hartley, Life Technologies, Inc). It involves incorporating into the amplification product a ribonucleoside triphosphate (rNTP) or deoxyribonucleoside triphosphate (dNTP) base that is not generally found in the sample to be analyzed: for example dUTP in the case of DNA analysis. The amplified product will thus have a sequence that has Uracil in multiple positions. The enzyme uracil DNA glycosylase (UDG) is added to samples prior to amplification. This will cause digestion of any contaminating reaction product (containing Uracil) without affecting the natural DNA in the sample.

This method will work for PCR but has limited potential for LCR. It can not be applied to blunt end LCR, and has a very limited potential for gap LCR. In gap LCR, it is not practical to incorporate more than a few uracil bases to fill the gap. Action of UDG will be at one site only, as opposed to a large number of sites in PCR amplification. Although this method has been commercialized by Roche Diagnostics as a way of inactivation of Amplicor™ DNA amplification assays, it cannot be applied to a variety of amplification reactions.

Other methods used to minimize the risk of contamination include the destruction of the amplified reaction product as well as any polynucleotide reagents after completion of the detection reaction. Such a method has been described by Celebuski in co-owned U.S. patent application Ser. No. 07/863,622, entitled "Methods for Inactivating Nucleotide Sequences and Metal Chelates for use Therein", filed Apr. 3, 1992. The inactivation method utilizes a divalent metal chelate such as copper phenanthroline complex and a dilute solution of hydrogen peroxide added to the reaction products and optionally to all equipment. This composition is very effective at cleaving all DNA into small fragments that are incapable of amplification. Accordingly, it is used after detection of amplification product, rather than prior to amplification.

Chemical measures such as UDG and metal chelates are effective in preventing minor contamination, but are less satisfactory in the case of major contamination involving droplets of reaction product. Thus the need to perform the amplification reaction in a closed system has been realized in the art in such documents as EP 0 381 501 A2, EP 0 550 090 A1 and U.S. Pat. No. 5,229,297. These documents describe such closed-reaction disposables.

Each of the patents, patent applications and literature documents specifically cited above or below is incorporated herein in its entirety by reference.

With these limitations of prior art, it is thus an important object of the invention to seek amplification reaction vessels and methods of use that will minimize contamination risk. A further object is to provide a disposable reaction vessel and method whereby an amplified reaction sample can be removed without removing a sealing cap; since cap removal tends to spread aerosol contamination. A further object of the invention is to provide a sealed disposable reaction vessel and method whereby an amplified reaction sample can be withdrawn with minimal disturbance to the seal of the vessel.

Another object of the invention is to provide a formulation that is suitable for unit dose preparation of reaction vessels such as the one described herein.

Yet another object of the invention is to provide a reaction vessel that is at once compatible with commercial thermal cyclers, for example the Perkin-Elmer 480, as well as with automated detection instrumentation such as those utilizing Microparticle Enzyme ImmunoAssay (MEIA) technology.

These and other objectives are met in the present invention as described below.

SUMMARY OF THE INVENTION

In a first aspect, the invention relates to a method for amplifying and detecting nucleic acid materials comprising the steps of:

a. adding a sample suspected to contain a target nucleic acid material to an amplification vessel along with labeled reagents for amplification of said suspected target nucleic acid to form a reaction mixture;

b. sealing the reaction mixture inside said vessel by closing a tightly sealing cap having a membrane that is penetrable by a pipettor probe;

c. amplifying the target nucleic acid material within said vessel;

d. removing a portion of the reaction mixture from said vessel for detection; and e. detecting the presence of amplified target nucleic acid by detection of said labeled reagents;

wherein said removing is effected by piercing said cap membrane with a pipettor probe, aspirating said portion of the reaction mixture into said pipettor and dispensing said portion in a distinct detection compartment without uncapping said vessel, thereby avoiding drops or aerosols of the amplified material which might contaminate the environment, unreacted samples or reagents.

The amplification method may be PCR or LCR or another amplification process.

The method preferably further comprises inactivating all nucleic acid material left in the vessel and in the detection compartment by dispensing thereto a nucleic acid inactivation reagent from a pipettor. The inactivation may include the consecutive addition of a copper phenanthroline chelate and hydrogen peroxide solution.

Preferably the reaction vessel is a tube having a cap with a membrane ranging from 0.002 to 0.015 inches, more preferably from 0.005 to 0.009 inches.

The pipetting probe may be a thin metallic tube with a chiseled edge, preferably having an outer diameter that does not exceed 0.050 inches.

Typically, the sealed amplification vessel is used in an automated pipettor probe instrument for automated detection, and said removing and detecting steps are both performed by the automated instrument. More preferably, the method further comprises a step of inactivating all nucleic acid material left in the vessel and in the detection compartment and said removing, detecting steps and inactivating steps are all performed by the automated pipettor instrument.

In a second aspect, the invention relates to stable compositions for PCR or LCR amplification reactions that omit magnesium ions from the composition. The compositions are typically used to fill unit dose reaction vessels. For example, a composition for preparing unit dose reaction vessels for amplification by the polymerase chain reaction (PCR), consists essentially of:

at least a pair of oligonucleotide primers for amplification by PCR of a desired target nucleic acid, each primer being present at above 1.6 nM, preferably between 1.6 nM and 160 nM;

a supply of deoxynucleotide triphosphates (dNTPs), present at above 1.0 μM, preferably between 1.0 and 200 μM;

a reagent having a thermostable polymerase activity, preferably a polymerase enzyme from a Thermus species organism;

optionally, detergents and inert carrier nucleic acid; and a concentration of $Mg^{2+}$ ions that is sufficiently low, preferably zero, to effectively disable said polymerase activity.

Another composition for preparing unit dose reaction vessels for amplification by the ligase chain reaction (LCR) or gap ligase chain reaction (GLCR), said composition consists essentially of:

at least two pairs of complementary oligonucleotide probes for amplification by LCR or GLCR of a desired target nucleic acid, each probe being present at above about 1.6 nM, preferably between 1.6 nM and 16 nM;

a reagent having a thermostable ligase activity, preferably a ligase enzyme from a Thermus species organism.;

optionally, a supply of less than all four deoxynucleotide triphosphates (dNTPs), present at above 1.0 μM and a reagent having a thermostable polymerase activity, preferably from a *Thermus sp.* polymerase enzyme;

optionally, detergents and inert carrier nucleic acid; and a concentration of $Mg^{2+}$ ions that is sufficiently low, preferably zero, to effectively disable said ligase activity.

Most preferably, the composition does include dNTPs and a reagent having a thermostable polymerase activity for performance of gap LCR.

In final aspects, the invention relates to sealable disposable devices for use in amplification reactions, as follows:

A reaction vessel device for performing a nucleic acid amplification assay comprising:

a tube of thermally stable polymeric material having an outer diameter dimensioned to fit into a thermal cycling apparatus, said tube having an opening to an interior;

a cap for tightly sealing the opening of the tube, said cap including a puncturable membrane of not more than 0.0015 inches thickness, whereby the membrane allows sampling the amplified reaction product from the closed tube with an automated pipettor without opening the tube; and a flexible hinge that holds the cap to the tube and permits folding of the cap into the opening.

Preferably the thickness of the puncturable membrane is between 0.002 and 0.015 inches; especialaly between 0.005 and 0.009 inches.

A reaction vessel device for performing a nucleic acid amplification assay comprising:

a tube of thermally stable polymeric material having an outer diameter dimensioned to fit into a thermal cycling apparatus, said tube having an opening to an interior;

a cap for tightly sealing the opening of the tube, said cap including a thin puncturable membrane, whereby the membrane allows sampling the amplified reaction product from the closed tube with an automated pipettor without opening the tube; and a flexible hinge that holds the cap to the tube and permits folding of the cap into the opening, wherein said hinge comprises a bi-fold hinge.

Preferably the thickness of the puncturable membrane is between 0.002 and 0.015 inches; especialaly between 0.005 and 0.009 inches.

The reaction vessel may have a hinge which defines a maximum radius of the closed tube and the distance from the outer diameter of the tube to said maximum radius is less than about 0.154 inches. Optionally the bifold hinge further comprises two grooves cut into the hinge material and the ratio g/h is about 0.8±20%, where g is the distance between the centerlines of the two grooves, preferably between 2 and 2.5 mm, and h is the total height of the hinge assembly from the point of attachment to the tube to the top of the cap measured when the cap is in a sealed position.

BRIEF DESCRIPTION OF THE FIGURES

FIG. 1 is a longitudinal cross section of a prior art SlickSeal™ disposable reaction vessel with the flip cap open.

FIG. 2 is a longitudinal cross section of a disposable reaction vessel in accordance with the present invention. It is shown with the flip cap open and the section is taken along the line a–a' of FIG. 3.

FIG. 3 is a top plan view of the reaction vessel of FIG. 2.

FIG. 4 is a side plan view of the reaction vessel of FIGS. 2 and 3.

FIG. 5 is a composite partial side view of the reaction vessels of FIG. 1 (top) and FIG. 2 (bottom), both shown with the flip cap in the closed position to illustrate the hinge structure.

DETAILED DESCRIPTION OF THE INVENTION

Figure 6:
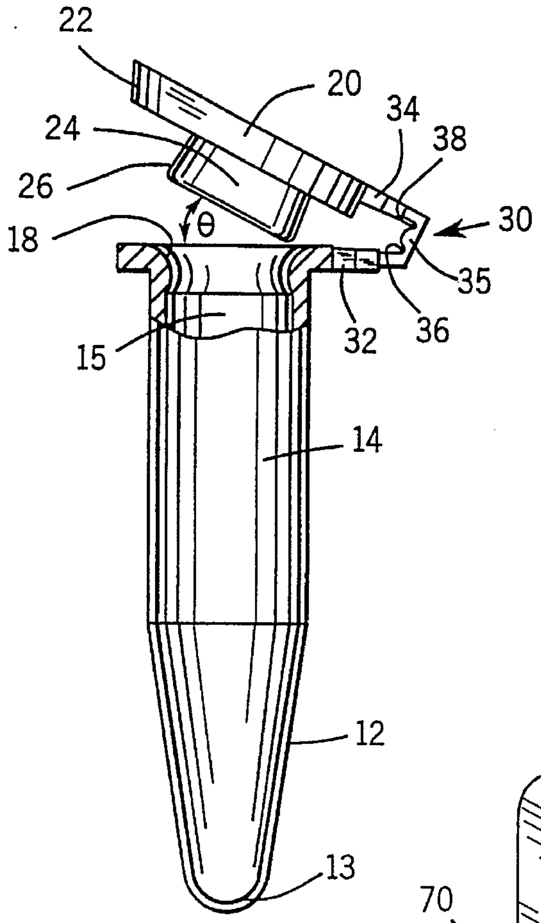
FIG. 6 is a side plan view of the reaction vessel of FIG. 2, partially cut away to cross section for clarity and showing the flip cap in a partially closed position.

This invention is a disposable reaction vessel for performing nucleic acid amplification assay. The disposable reaction vessel has a penetrable cap, that can be penetrated by an automated pipettor to aspirate a portion of an amplified reaction product. The disposable reaction vessel contains the reagents necessary to perform a nucleic acid amplification assay such as a Ligase Chain Reaction (LCR) or a Polymerase Chain Reaction (PCR). A patient specimen is added to the unit dose reagents in the disposable reaction vessel and the penetrable cap is closed. The disposable reaction vessel containing the reaction mixture and the specimen undergoes amplification, typically by placing it in a thermal cycler. After amplification the intact disposable reaction vessel is transferred to an automated analyzer where an automated pipettor penetrates the closure membrane and aspirates a portion of the amplified sample for further processing, without removal of the reaction vessel cap. This avoids the generation of potentially contaminating aerosols or droplets.

1. Definitions:

An "amplification reaction" is a reaction in which multiple copies of an original nucleic acid sequence are generated, typically by repeating an enzymatic duplication process for a number of cycles. When additional copies can be made from each of the duplicate copies made in an earlier cycle, the amplification process is said to be exponential with respect to the number of cycles. While exponential amplification is desirable to improve assay sensitivity, this heightened degree of sensitivity is also a drawback if the amplification products are not carefully contained, resulting in contamination. Issues of contamination and several amplification methods are specifically mentioned in the Background.

Some amplification reactions, for example PCR and LCR, involve cycles of alternately high and low set temperatures, a process known as "thermal cycling". PCR or "Polymerase Chain Reaction" is an amplification reaction in which a polymerase enzyme, usually thermostable, generates multiple copies of the original sequence by extension of a primer using the original nucleic acid as a template. PCR is described in more detail in U.S. Pat. Nos 4,683,202 and 4,683,195. LCR or "Ligase Chain Reaction" is a nucleic acid amplification reaction in which a ligase enzyme, usually thermostable, generates multiple copies of the original sequence by ligating two or more oligonucleotide probes while they are hybridized to the target. LCR, and its variation, Gap LCR, are described in more detail in EP-A-320-308 (Backman et al), EP-A-439-182 (Backman, et al) and WO 93/100447 (Birkenmeyer et al.) and elsewhere.

"Thermal cycler" is a device used to heat, cool and/or hold a nucleic acid amplification reaction mixture between or at a set temperature for a set time duration.

"Unit dose" refers systems wherein a single reaction vessel contains all or nearly all the reagents needed to accomplish a reaction except for the sample itself. Generally the user has only to add the sample and start the reaction. Typically, unit dose reaction vessels are disposable, and are discarded after a single use.

2. Reaction Vessel:

The reaction vessel 10 of the present invention is shown in FIGS. 2 to 6. The reaction vessel 10 is alternately referred to herein as a "tube", a "disposable", and a "vessel", which terms are used interchangeably. Since many portions of the prior art tube are similar, they are described using the same reference numeral appended with an "a"; e.g. the prior art tube of FIG. 1 is designated 10*a*.

The vessel includes a longitudinal barrel comprising a conical tapered bottom portion 12 having a closed end 13, and a cylindrical portion 14. The taper and length of the tapered portion 12 are adapted to fit into a commercial thermal cycler heating block (not shown). For example the taper is about 9° off the centerline; the height of the tapered portion 12 is about 13 mm and the diameter at the widest point of the tapered portion 12 is about 7 mm. These dimensions are in no way critical to operation of the device. They merely facilitate a close fit into a commercial thermal cycler, such as the Perkin Elmer 480. Good fit in the thermal cycler and thin tube walls promote more efficient transfer of heat energy between the heating block and the reaction mixture. Generally the tube walls are less than about 0.040 inches, preferably less than about 0.030 inches. The particular embodiment described herein calls for walls of 0.024±0.004 inches.

The vessel barrel also comprises a cylindrical portion 14 joined with the tapered portion. The cylindrical portion bears the same outer diameter as the widest part of the tapered portion, namely about 7 mm in the preferred embodiment. The length of the cylindrical portion is not crucial and is governed by the volume needed in the interior of the vessel, by the height and type of cap mechanism, and by whether or not some type of lid is used on the thermal cycler. The overall length may range from about 5 to 30 mm, preferably 10 to 20 mm. In the preferred embodiment the cylindrical portion 14 is about 17 mm long to permit the affixing of a label, such as a bar code label, to the vessel barrel.

The upper end of the cylindrical portion 14 flares radially outwardly to define an opening 16. Together the tapered portion 12 and the cylindrical portion 14 define an interior 15, into which reaction sample and reagents may be placed. The opening 16 includes a radiused edge 18 for easy and tight sealing with the cap 20.

The cap 20 includes a tab means 22 to facilitate opening and closing of the cap. The cap further includes a generally cylindrical sealing member 24 having an outer circumference 26 adapted to fit tightly into the opening 16 and to create an effective seal against the radiused edge 18 or the interior wall just below the radiused edge. For this reason, the sealing member 24 may be slightly tapered as best shown in FIGS. 2 and 4 to have a larger outer circumference 26 at the end furthest from the cap body 20.

Closing one end of the cylindrical sealing member 24 is a top cover. In FIG. 2 this is shown as the thin membrane 28; while in FIG. 1 the prior art cover is shown as 29 since it differs significantly from the membrane 28 of the invention. The purpose of the cover 29 of the prior art tube is merely to close the chamber off to prevent leakage of its contents. Therefore it is molded of the same material and approximately the same thickness as the rest of the walls of the tube 10*a*. In contrast, the membrane 28 of the vessel 10 according to the invention is significantly thinner so that it may be pierced by an instrument probe as described in connection with the methods described below.

Although the preferred cover 28 is 0.005±0.001 inch (0.125±0.025 mm) thick, the thickness may range from 0.002 to 0.015 inch (0.05 to 0.375 mm), preferably 0.002 to 0.01 inch (0.05 to 0.25 mm) and more preferably 0.005–0.009 inch (0.125 to 0.225 mm). In essence the membrane 28 must be strong enough not to tear or rupture during normal handling, but not so strong as to resist puncture by the instrument probe. Thus, the maximum strength/thickness is governed by the tensile strength of the membrane composition, the geometry of the membrane support, and the strength and downward thrust force of the particular instrument probe. These criteria are highly dependent on tube composition and on the instrument system in use. The presently preferred thickness was selected for Himont PD701 resin (Himont USA, Inc., Wilmington, Del.) subjected to not more than 900 grams force by a 0.040 inch diameter stainless steel probe with a 45 degree beveled tip in a modified IMx® instrument (see section 4 below). Evaluation and optimization of these parameters with other compositions or in other instrument systems is easily within the ability of one of ordinary skill in this art.

A hinge, shown generally as 30 in FIG. 2 and 31 in FIG. 1 holds the cap 20 to the barrel of the vessel via a thin, flexible isthmus. The hinge 30, 31 keeps the cap 20 handy but has sufficient flexibility to permit folding of the hinge back on itself to permit insertion of the cylindrical sealing member 24 into the opening 16 of the tube. It will be realized immediately that a tight seal between outer circumference 26 and tube opening 16 requires closely matched tolerances between these parts, and that any such hinge has a flexing tendency to dislodge the cap from the tube opening. Given the close fit of these parts it will also be apparent that the most facile insertion of the cap will occur when the sides of the cylindrical seal 24 are approximately parallel to the walls of the longitudinal portion 14, or in other words, when the "angle of attack" $\theta$ (see FIG. 6) is approximately zero. Thus, there is a trade-off of considerations in hinge construction. On the one hand it is desirable to minimize the material of the hinge and to keep the cap body 20 close to the tube barrel 14, but this causes the cap seal member 24 to enter the opening 16 at a severe and non-optimal angle of attack $\theta$, as shown in FIG. 6. On the other hand, optimizing the angle of attack requires that a much longer hinge section be used, thus wasting material and increasing the magnitude of the effective maximum radius of the reaction vessel.

The present invention overcomes these trade-off problems by providing a novel "bi-fold" hinge 30, which differs significantly from the prior art hinge 31. A "bi-fold" hinge is characterized by the presence of two or more fold locations or "corners", the sum of the angles of the these folds being approximately 180 degrees since that is the arc through which the cap must fold back in order to seal the tube. The hinge 30 includes an extension 32 of the flared portion of the longitudinal portion 14 and an extension 34 of the cap body 20. The two extensions 32 and 34 are separated by grooves 36 and 38, respectively, from a central spine ridge 35. The two grooves are spaced a distance g from one another (see FIGS. 2 and 3). As best shown in FIG. 5, the bi-fold construction permits two (or more) flex points at the grooves 36, 38 and facilitates a more favorable angle of attack while actually decreasing the effective overall radius by the amount d in FIG. 5. In the actual embodiments from which FIG. 5 was generated, d is approximately 0.02 inches.

The distance x represents the maximum amount by which the hinge extends beyond the outside of the barrel portion 14 when the cap is in the closed position. It is assumed that the cap tab 22 extends no further than the hinge 30 so that the hinge represents the maximum overall radius. In the preferred embodiment of the invention, x is less than or equal to about 0.154 inches, preferably about 0.149 inches. The distance r is another measure of effective overall radius, but r will vary with the diameter of the cylindrical portion 14.

The distance h is the total height of the hinge assembly with the cap closed, including the cap body 20 and the outwardly turned flange of cylindrical portion 14 where the hinge attaches to the tube. It is typically approximately the same height as the spine region 35. The distance h is also related to the distance g between the two grooves 36 and 38. In the preferred vessel shown, h is about 0.103 inches; and the distance g is about 0.087 inches. Thus, the ratio g/h of the present embodiment is 0.84, but may vary by as much as 20%, preferably not more than about 10% from a ratio of 0.8. As seen in FIG. 5, when the extensions 32 and 34 are approximately equal, the spine 35 becomes substantially perpendicular to the extensions and parallel to the longitudinal axis of the tube barrel, each flex point or "corner" defining approximately a 90 degree angle.

Ratios of g/h that are much greater than about 0.8 tend to correspond with differences in length of the extensions 32 and 34 to produce one acute and one obtuse angle in the "corners". This also tends to produce angled spines 35.

The disposable vessel 10 of this invention is made of a polymeric material that is inert with respect to interaction with components of the reaction mixture or the products of the amplification reaction. The material should be somewhat flexible to permit hinge operation and penetration of the membrane 28 by the probe, and preferably autoclavable. A preferred polymer is polypropylene, from which the entire device, including the membrane 28 can be molded. Many grades of polypropylene are commercially available. A resin like Himont PD701 natural (Himont USA, Inc., Wilmington, Del.) is preferred as it exhibits sufficient inertness and flexibility and can be autoclaved. The entire device can be injection molded although high injection pressures and/or a technique known as "coining" may be required to achieve uniform filling of the cavity in the area of the thin membrane 28.

Mold release compounds such as silicone oil or mineral oil may be used, but it is important to avoid mold release compounds containing divalent ions such as magnesium or zinc stearate or palmitate, where such ions affect the activities of the enzymes used in the amplification process.

3. Methods of Use:

The reaction vessels described above are useful in amplification reactions, particularly thermal cycling amplification reactions, where a great quantity of potentially contaminating nucleic acid is created. A preferred method of this invention is the use with LCR reactions, and this will be described in detail herein, but it should be realized that the methods are equally useful with other amplification methods.

In accordance with the preferred method, the reaction tubes are first placed in an amplification instrument, such as a thermal cycler, and are incubated at (an) appropriate temperature(s) for a predetermined time. LCR utilizes a set of four probes in two complementary pairs, the pairs lying substantially adjacent one another when hybridized to the target. A ligase enzyme, preferably thermostable, covalently joins the adjacent probes. After separation, the joined probes serve as template or target for the complementary probes in a subsequent cycle. Typical denaturation temperatures range from 75°–90° C. and typical annealing temperatures range from 50°–65° C., depending on probe melt characteristics as is known in the art.

In a particularly preferred variation, the tubes are "unit dose" disposable tubes, meaning that they contain premeasured suitable quantities of the four probes, buffers, and ligase or other enzymes. Typically only the patient sample needs to be added to the reaction tube. However, in one variation, it has been found that omission of divalent metal ions, especially $Mg^{2+}$. from the unit dose composition can prolong stability and reduce the incidence of target-independent background ligation events. A typical unit dose tube contains about 100 μL of LCR or PCR reaction mixture. For PCR this comprises a mixture of primers for flanking the target sequence to be amplified (preferably at least one primer is labeled for detection), deoxynucleotide triphosphates (dNTPs), thermostable polymerase, non-interfering DNA such as salmon sperm DNA, detergents and buffer. For LCR the composition typically comprises LCR probes that are specific for the target sequence being detected, thermostable ligase, non-interfering DNA such as salmon sperm DNA, NAD, detergents and buffer. In the case of Gap LCR, specific dNTPs, and thermostable polymerase are also present. In both PCR, LCR and GLCR, however, it is preferable to omit the cofactor $Mg^{2+}$ ions, which may be added along with buffer for the sample. The concentration of $Mg^{2+}$ ion in the unit dose formulation should be zero or at least low enough that it is insufficient to enable the activity of the enzyme.

The unit dose reagent tubes are stored closed in their boxes below room temperature, preferably at 2°–8° C. or frozen, but are allowed to equilibrate to room temperature prior to use. The unit dose tube is opened and a 100 μL of pretreated sample specimen is added to it (for a total reaction volume of about 200 μL).

Biological specimens to be tested by these methods include endocervical swabs, urethral swabs, urine, blood, smears, skin and hair extracts and the like.

The tube is then closed and transferred to a thermal cycling apparatus such as the Perkin-Elmer 480 nucleic acid cycler where the amplification reaction takes place. A particularly preferred method and system for transporting the tubes from a workstation to the thermal cycler (and back again) is disclosed in co-owned U.S. application Ser. No. 08/141,243, now abandoned, filed on even date herewith, entitled Tube Transport System and Method of Use, which is incorporated herein by reference.

After amplification, the tubes are transferred to a detection apparatus. A preferred method of detection is the use of microparticle capture enzyme immunoassays (MEIA) for the detection of the amplification products. MEIA is as described by Fiore, et al, *Clin. Chem.* 34(9): 1726–1732 (1988) and in EP-A-288 793, and a commercial clinical analyzer that utilizes this method is the IMx® instrument, marketed by Abbott Laboratories (Abbott Park, Ill.). For MEIA detection of amplification products, both capture haptens (hapten1) and detection haptens (hapten2) must be associated (e.g. covalently attached to) each amplification product. The incorporation of haptens into LCR or PCR reaction products is known in the art, for example from EP-A-0 357 011 and EP-A-0 439 182. Briefly, the method employs primers (in a PCR reaction) which have reactive pair members linked to them. The reactive pair members can be attached to a solid phase and/or detected by labeled conjugates. Reactive pairs were selected from the group of hapten and antibody, biotin and avidin, enzyme and enzyme receptor, carbohydrate and lectin, and pairs of complementary DNA strands.

Many different haptens are known, and virtually any hapten can be used with the present invention. Many methods of adding haptens to probes are known in the literature. Enzo Biochemical (New York) and Clontech (Palo Alto) both have described and commercialized probe labeling techniques. For example, a primary amine can be attached to a 3' oligo end using 3'-Amine-ON CPG™ (Clontech, Palo Alto, Calif.). Similarly, a primary amine can be attached to a 5' oligo end using Aminomodifier II® (Clontech). The amines can be reacted to various haptens using conventional activation and linking chemistries. Alternatively, a label-phosphoramidite reagent is prepared and used to add the label to the oligonucleotide at any position during its synthesis. For example, see Thuong, N. T. et al., *Tet. Letters,* 29(46):5905–5908 (1988); or Cohen, J. S. et al., U.S. patent application Ser. No. 07/246,688, filed Sep. 20, 1988, abandoned (NTIS ORDER No. PAT-APPL-7-246,688) (1989).

Some illustrative haptens include many drugs (e.g. digoxin, theophylline, phencyclidine (PCP), salicylate, etc.), T3, biotin, fluorescein (FITC), dansyl, 2,4-dinitrophenol (DNP); and modified nucleotides such as bromouracil and bases modified by incorporation of a N-acetyl-7-iodo-2-fluorenylamino (AIF) group; as well as many others. Certain haptens described herein are disclosed in co-owned patent applications U.S. Ser. No. 07/808,508 (adamantaneacetic acids), U.S. Ser. No. 07/808,839 (carbazoles and dibenzofurans), both filed Dec. 17, 1991 and abandoned; U.S. Ser. No. 07/858,929 (acridines), and U.S. Ser. No. 07/858,820 (quinolines), both filed Mar. 27, 1992 and abandoned (collectively referred to herein as the "hapten applications").

The closed unit dose vessel containing the amplified product of the LCR (or PCR or other) amplification reaction is transferred to a wedge shaped holder of a modified IMx® analyzer. The wedge and modifications to the IMx analyzer are described below.

Within the instrument, a hollow-bore probe on a robotic arm is guided by a microprocessor and suitable software into position above the reaction vessel and the probe is lowered into the vessel by rupturing the membrane 28. Upon reaching the sample fluid, the probe aspirates a predetermined volume of amplified reaction mixture and automatically transfers it to an associated incubation well, where it is incubated with MEIA capture phase comprising microparticles coated with anti-hapten1 antibodies. The transfer of the reaction product from the amplification tube to the incubation well is effected without opening the tube and without the potential of spilling the reaction mixture or the formation of aerosols. This in turn considerably decreases the potential of contaminating non-reacted samples with the amplifiable amplification product.

The probe moves to a wash station for cleansing before another reaction vessel is penetrated, and this procedure continues until all reaction tubes have been sampled and are incubating. This wash procedure avoids carryover contamination from one sample to the next. After incubation, a portion of the microparticle suspension is aspirated by the probe and deposited on the glass fiber matrix of an associated detection cell, where the particles are separated from the rest of the solution and retained on the matrix. The captured particles are washed and an enzyme label conjugate (alkaline phosphatase coupled to anti-hapten2) is added and incubated as is usually practiced in an IMx® assay. The incubated capture microparticles/amplified product/conjugate complex captured on the matrix is washed and then a substrate for the enzyme label of the conjugate is added. The presence of the analyte DNA is detected from measuring the rate of generation of a fluorescence signal from conversion of the substrate 4-methyl umbelliferyl phosphate to the fluorescent 4-methylumbelliferone.. The "rate" of substrate turnover is expressed in counts/sec/sec (c/s/s) and a "machine noise" background of 8–12 c/s/s is typical.

After detection is complete, the probe preferably dispenses a chemical inactivation reagent to all areas of the incubation well, the detection cell and the reaction tube. This chemically destroys all DNA present to eliminate inadvertent contamination of future samples or reagents. A suitable copper phenanthroline chemical inactivation composition is described in co-owned U.S. patent application Ser. No. 07/863,622, entitled "Methods for Inactivating Nucleotide Sequences and Metal Chelates for use Therein", filed Apr. 3, 1992.

Figure 7:
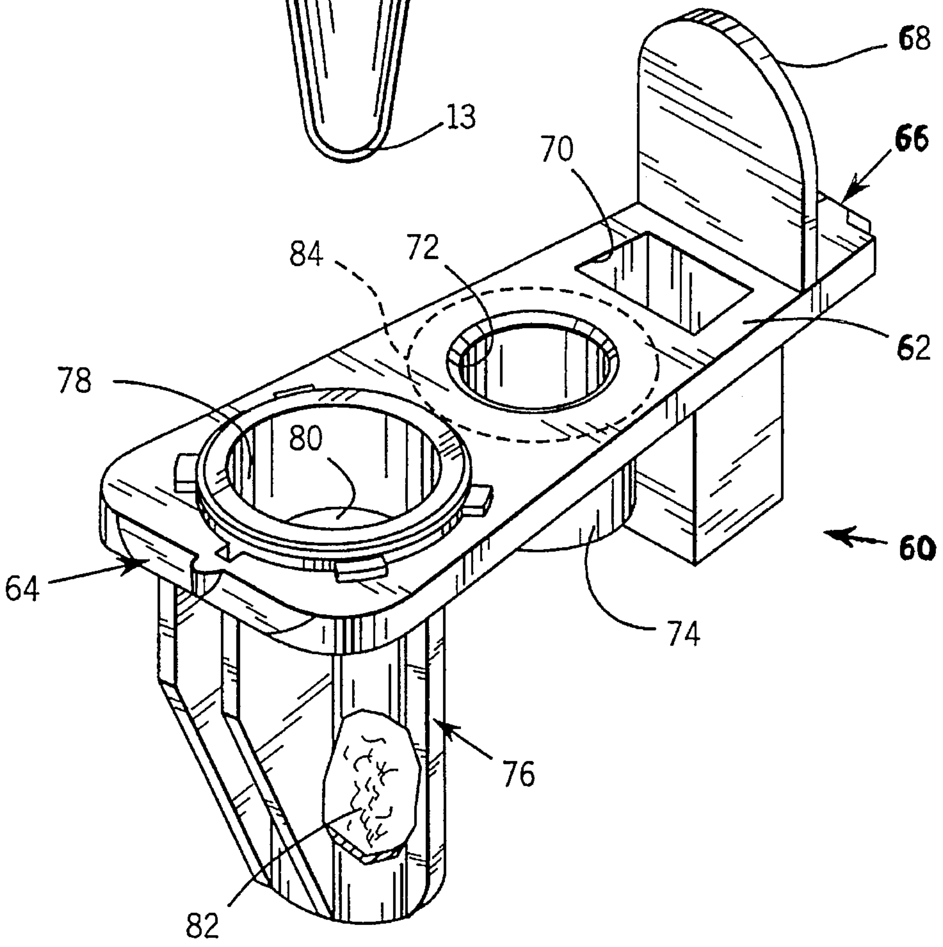
FIG. 7 is a top perspective view of a reaction vessel holder adapted to hold the reaction vessel of FIG. 2 for use in an automated detection apparatus.

4. Reaction vessel holder and modifications to the IMx® analyzer:

Another aspect of the invention relates to the vessel holder 60 of the reaction tube, which may be made of any suitable plastics material having sufficient rigidity to support the structures with dimensional stability. Exemplary plastics are polycarbonates and polystyrenes, such as ABS or styrene-acrylonitrile (SAN). The holder is depicted in FIG. 7. It contains a substantially planar base 62 which is wider at one edge 64 than at the other edge 66. This produces trapezoidal or wedge shape adapted such that several (20–40) of them will fit in sectors of a circular carousel (not shown). The base includes a molded tab 68 at the radially inward end for easier grasping.

Molded into the base 62 are three structures. The precise shape of none of these structures is critical; they need only have sufficient volume for the purpose stated below and be configured not to interfere with seating of the wedge in the carousel. The first structure is adjacent the tab 68 and is a well 70, rectangular in the embodiment shown. The well 70 has a closed bottom and is adapted for holding and incubating a reaction mixture. The next structure is an aperture 72 near the center of the wedge. It preferably is reinforced with downwardly extending side walls 74, cylindrical in this case. The aperture 72 is adapted to receive the reaction vessel described above. The area of the aperture should correspond to and be only slightly larger than the cross sectional area of the reaction vessel so that the reaction vessel does not move around significantly in the holder.

The third structure is a detection cell or compartment 76. The detection cell is virtually identical to the detection cell of the commercial IMx® instrument. It includes an angled funnel-like structure 78 for holding the initial deposit of a reaction sample; a reaction matrix 80, typically glass fiber, at the bottom of the funnel; and an absorbent member 82 disposed below the reaction matrix (shown inside cell 76 via a partially cut-away view in FIG. 7). As in the IMx® instrument, the detection cell 76 collects the capture microparticles in the glass fiber matrix 80 and permits passage of liquid reagents and wash solutions through the matrix 80 into the absorbent member 82.

The holder 60 may also include means for attaching and locking the holder into a carousel, as well as reinforcing webbing between the downwardly extending structures 70, 74 and 76.

The modified vessel holder 60 differs from the prior art IMx® wedge because of the aperture 72 adapted for receiving the reaction tube. The IMx® wedge includes one or more additional sample wells in this location instead of the aperture, and is not adapted to receive and additional physical structures or components.

It will be realized in the case of a cylindrical reaction tube 10 and corresponding round aperture 72 that the reaction tube may rotate in the base 62. Since one or the other of the cap tab means 22 and hinge 30 typically defines a point of maximum radius, it is preferable to insure that the arc swung by these points (shown in dotted line at 84 in FIG. 7) defines a clear path so that the tube may rotate freely in the aperture.

The hardware modifications made to the commercial IMx® instrument included the following. Software modifications accompanied some changes but are easily optimized by those skilled in the art and are not described herein. An instrument so modified is referred to herein as an LCx™ instrument.

1) The automated pipettor mechanism was reinforced to permit penetration of the membrane seal 28 on the disposable amplification tube 10 without damaging the probe. These changes were: strengthening the guide rods, adding a guide rod and a top cross rod.

2) A single tip pipetting probe, about 0.040 inches in diameter, made of stainless steel and chiseled at 45 degree angle for ease of penetrating the membrane seal.28, replaced the standard pipette and electrode of the IMx.

3) Use of a single tip probe necessitated abandonment of the conductance mode liquid level sense apparatus. Instead a capacitance level sense mechanism was adopted, requiring that the pipetting probe act as a transmitter and that receiver plates were positioned under the reagent pack and the carousel. Such capacitance level sense arrangements are known in the art.

4) The wash station for the probe was made deeper to permit washing more of the probe tip. Since the probe penetrates the membrane seal 28, it was possible to accumulate contamination higher up on the probe tip from the underside of the membrane.

5) A tube retainer mechanism was added to retain the tube 10 seated in the holder 60 as the probe tip is being withdrawn from the vessel. The retainer comprises a rotatable pedestal from which a boom arm can swing into position over the reaction tube at the position where the probe is to be withdrawn. The boom arm includes a slot or an opening through which the probe passes, as well as a deflector portion that contacts the tube cap 20 to keep the tube in position in the holder 60.

6) The FPIA diluent buffer bottle is replaced with a bottle containing inactivation diluent (5% hydrogen peroxide solution) and the software is altered to permit access to both the standard MEIA diluent and the inactivation diluent.

EXAMPLES

Example 1. Penetrable Cap Tubes

An injection mold was constructed for molding tubes as shown in FIGS. 2–4. The resin used was Himont PD701 natural (Himont USA, Inc., Wilmington, Del.) without any additive or mold release compounds. During molding, the membrane area was coined to achieve more uniformity in thickness in the penetrable membrane, which was controlled to 0.005±0.001 inches. The tubes were sterilized by autoclaving to get rid of possible nuclease contamination.

Example 2. LCx™ Instrument

An IMx® instrument was modified as described in section 4 above.

Example 3. *Chlamydia trachomatis* LCR Unit Dose Tubes

Reaction tubes according to example 1 were filled using a multiple pipettor or a repeater pipettor to dispense 100 μL of a master reagent into each tube, such that each unit dose reagent tube contained the following components in 2X LCR buffer (100 mM EPPS, 40 mM $K^+$ [from KOH and KCl], 200 μM NAD):

- a set of 4 Gap LCR probes specific for positions 6917–6964 of the *Chlamydia trachomatis* cryptic plasmid. These probe are described in detail in copending application U.S. Ser. No. 08/116,389 filed Sep. 3, 1993 (attorney docket 5372.US.01), each probe being present at $1.2\times10^{12}$ molecules/100 μL;
- 1 μg acetylated bovine serum albumin (BSA), 1.0 mM EDTA, and 0.04% by weight sodium azide,
- 3.4 μM dTTP and 3.4 μM dCTP (gap-filling nucleotides);
- 2 units of *Thermus sp* DNA polymerase; and
- 1,800 units of *Thermus thermophilus* DNA ligase.

No $Mg^{2+}$ (or $Mn^{2+}$) ion was present in the unit dose tubes. The caps of the tubes were closed and the tubes were stored at 8° C. until use.

Example 4. Experimental Procedure

100 μL of a *Chlamydia trachomatis* calibrator or a 1:2 dilution of the calibrator were pipetted into each of several unit dose tubes prepared according to Example 3. The amount of Chlamydia tDNA in the calibrator is estimated by standard curves to be equivalent to 2.0 inclusion forming units per 100 μL; the negative control was 150 ng salmon sperm DNA. $MgCl_2$. was added as an activation reagent to a final concentration of 30 mM (in 200 μL). For actual test samples, the $Mg^{2+}$ is supplied in the specimen transfer buffer and is added to the unit dose tube with the sample.

The tubes were placed in a Perkin Elmer 480 thermal cycler. Cycling conditions were: 97° C. for 1 second; 55° C. for 1 second; and 62° C. for 50 seconds for a total of 40 cycles.

After completion of the thermal cycling process, the tubes were transferred to the LCx™ instrument. Each tube was mounted in a holder (wedge) placed on the carousel, the carousel was placed into the instrument. A sample tube retainer was engaged on top of the carousel to prevent the tubes from lifting up as the pipetting probe pulls out. A reagent pack was placed in the instrument. The reagent pack contained bottles of the following compositions: 1) anti-carbazole coated microparticles, 2) alkaline phosphatase-labeled anti-adamantane, 3) substrate methyl umbelliferyl phosphate, and 4) copper phenanthroline in Tris buffer.

The results are given in Table 1 for duplicate samples over four runs (n=8).

TABLE 1

LCR Chlamydia trachomatis assay results in a closed tube

| Sample type | Mean Signal (counts/s/s) | SD | Range |
|---|---|---|---|
| Negative control | 7 | 2 | 6–12 |
| Calibrator diluted 1:2 | 484 | 45 | 443–558 |
| Calibrator | 862 | 71 | 791–962 |

Example 5. Inactivation

The inactivation solution was 0.1M copper phenanthroline in tris buffer. The inactivation diluent was 5% hydrogen peroxide solution. The LCx™ instrument is programmed to pipette 50–60 μL of the inactivation solution into each of the incubation well, the reaction tube and the detection cell, followed by 60–80 μL of the inactivation diluent at each location on all wedges in the carousel.

Example 6: Specimen Processing and Results

Figure 8:
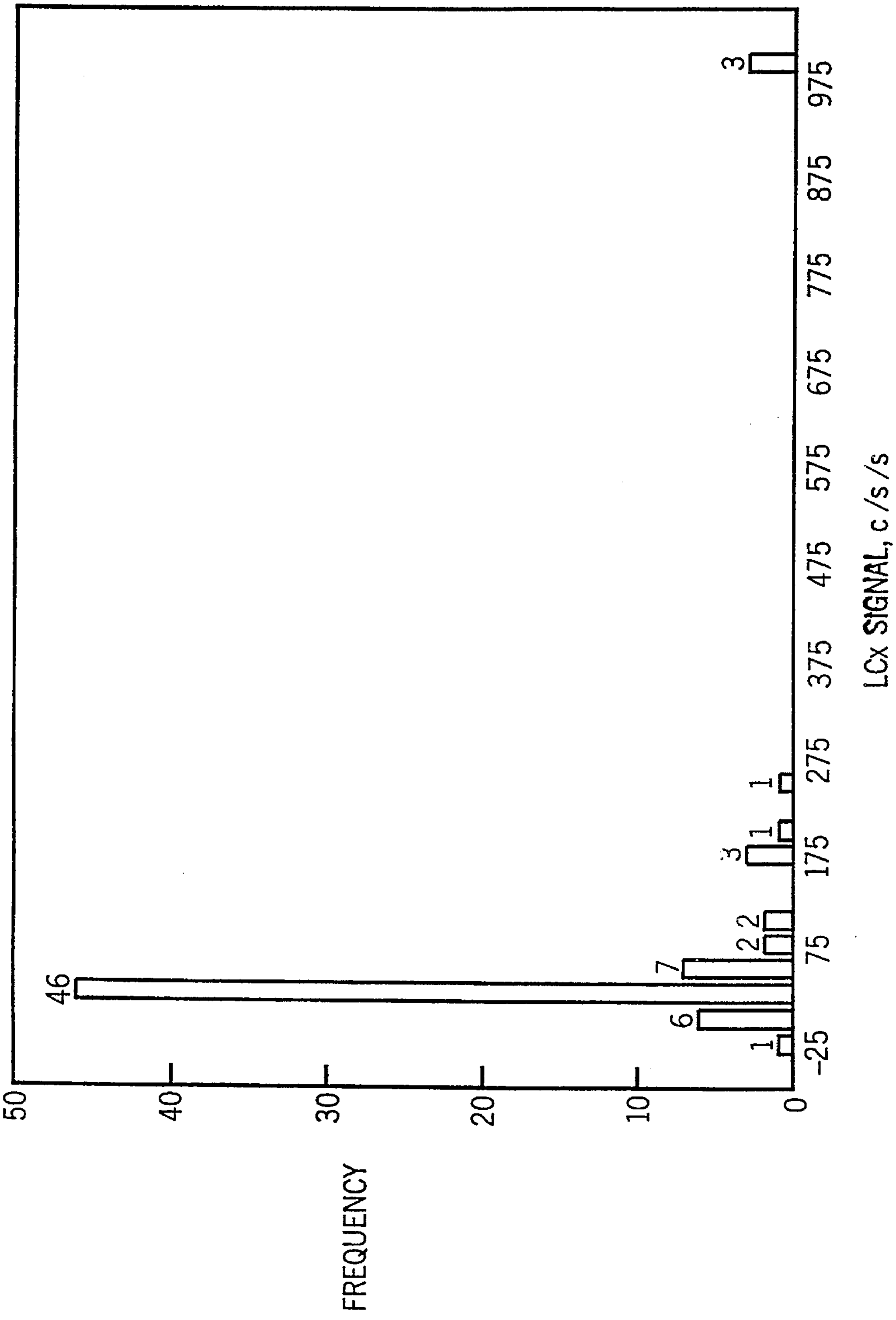
FIG. 8 is a graph of the result of example 6.

A population of 72 endocervical swabs tested for *Chlamydia trachomatis* by standard culture method were also tested by the procedure of example 4 using the reaction tubes of example 1. The specimens were diluted in a specimen buffer containing sufficient $MgCl_2$ to produce a final concentration of approximately 30 mM (in 200 μL). FIG. 8 shows a frequency distribution of the number of samples vs rate signal expressed as counts/sec/sec. The three samples that tested positive by culture gave signal higher than 500 counts/sec/sec. The 69 samples that tested negative by the culture method gave a mean signal of less than 30 counts/sec/sec. The mean of the negative population plus two standard deviations was less than 500 counts/sec/sec.

The examples shall serve only to illustrate various embodiments of the invention, but the scope for which protection is sought shall be defined by the appended claims.

What is claimed is:

1. In a method for amplifying and detecting nucleic acid materials comprising the steps of:

a) adding a sample suspected to contain a target nucleic acid material to an amplification vessel along with oligonucleotide probes or primers, at least one of which bears a detectable reporter group, for amplification of said suspected target nucleic acid to form a reaction mixture;

b) sealing the reaction mixture inside said vessel by closing a tightly sealing cap;

c) amplifying the target nucleic acid material within said vessel; and d) detecting the presence of amplified target nucleic acid by detection of said detectable reporter group;

wherein the improvement comprises i) providing said sealing cap with a membrane that is penetrable by a pipettor probe;

ii) removing a portion of the reaction mixture from said vessel for detection wherein said removing is effected by piercing said cap membrane with a pipettor probe aspirating said portion of the reaction mixture into said pipettor; and iii) dispensing said portion in a distinct detection compartment without uncapping said vessel, thereby avoiding drops or aerosols of the amplified material which might contaminate the environment, unreacted samples or reagents.

2. The method of claim 1 wherein the improved method further comprises inactivating all nucleic acid material left in the vessel and in the detection compartment by dispensing thereto a nucleic acid inactivation reagent from a pipettor.

3. The method of claim 2 wherein said inactivating comprises the consecutive addition of a copper phenanthroline chelate and hydrogen peroxide solution.

4. The method of claim 1 wherein the membrane has a thickness ranging from 0.002 to 0.015 inches.

5. The method of claim 4 wherein the membrane has a thickness ranging from 0.005 to 0.009 inches.

6. The method of claim 1 wherein the pipetting probe is a metallic tube with a beveled tip.

7. The method of claim 6 wherein the outer diameter of said probe does not exceed 0.050 inches.

8. The method of claim 1 wherein the amplifying step comprises a polymerase chain reaction.

9. The method of claim 1 wherein the amplifying step comprises a ligase chain reaction.

10. The method of claim 1 wherein the improved method further comprises a step of placing the sealed amplification vessel in an automated pipettor probe instrument for automated detection, said placing step being prior to the removing of step ii.

11. The method of claim 10 wherein said removing and detecting steps are both performed by the automated instrument.

12. The method of claim 10 further comprising a step of inactivating all nucleic acid material left in the vessel and in the detection compartment by dispensing thereto a nucleic acid inactivation reagent, wherein said removing, detecting steps and inactivating steps are all performed by the automated pipettor instrument.

* * * * *